United States Patent [19]

Warren, III et al.

[11] Patent Number: 5,051,356

[45] Date of Patent: Sep. 24, 1991

[54] SPECIFIC BINDING COMPOSITION COMPRISING A LOW PI PROTEIN OR CARBOHYDRATE AND A DIAGNOSTIC TEST KIT AND METHOD OF USE

[75] Inventors: Harold C. Warren, III, Rush; Brian A. Snyder, Rochester, both of N.Y.

[73] Assignee: Eastman Kodak Company, Rochester, N.Y.

[21] Appl. No.: 206,257

[22] Filed: Jun. 13, 1988

[51] Int. Cl.$^5$ .................. G01N 33/535; G01N 33/543; G01N 33/569

[52] U.S. Cl. ..................... 435/7.34; 435/7.92; 435/7.5; 435/962; 435/975; 436/501; 436/518; 436/808

[58] Field of Search ............. 435/7, 36, 7.1, 7.34, 435/7.9, 7.92, 968, 975; 436/533, 534, 529, 904, 501, 518, 808

[56] References Cited

U.S. PATENT DOCUMENTS

| | | | |
|---|---|---|---|
| 3,951,748 | 4/1976 | Devlin | 195/103.5 |
| 4,483,928 | 11/1984 | Suzuta et al. | 436/519 |
| 4,670,381 | 6/1987 | Frickey et al. | 435/7 |
| 4,812,414 | 3/1989 | Warren et al. | 436/533 |
| 4,828,978 | 5/1989 | Warren et al. | 435/36 |
| 4,828,980 | 5/1989 | Snyder et al. | 436/534 |
| 4,923,680 | 5/1990 | Nelson | 435/7 |
| 4,965,191 | 10/1990 | Warren III et al. | 435/7 |

OTHER PUBLICATIONS

A. Voller and D. E. Bidwell, Enzyme Immunoassays, pp. 77–86, Chap. 6 Alternative Immunoassays, Edited by W. P. Collins, John Wiley and Sons, 1985.

Robertson, P. W. et al., Reduction in Non-Specific Binding in Enzyme Immunoassay, Using Casein Hydrolysate in Serum Diluents, Journ. of Immun. Meth., 26 (1985), pp. 195–197.

*Primary Examiner*—Esther L. Kepplinger
*Assistant Examiner*—Carol E. Bidwell
*Attorney, Agent, or Firm*—J. Lanny Tucker

[57] ABSTRACT

A specific binding composition comprises a specific binding species and one or more water-soluble proteins or carbohydrates, substantially none of which has a pI greater than about 5. This composition provides improved sensitivity with lower background in diagnostic tests. Preferably, the species is labeled for detection, for example, with an exzyme. The composition can be included with a dye-providing composition in a diagnostic test kit for use in diagnostic methods.

18 Claims, No Drawings

SPECIFIC BINDING COMPOSITION COMPRISING A LOW PI PROTEIN OR CARBOHYDRATE AND A DIAGNOSTIC TEST KIT AND METHOD OF USE

FIELD OF THE INVENTION

This invention relates to a specific binding composition comprising a specific binding species, and to its use in a method for detecting a target ligand. It also relates to a diagnostic test kit including the composition. The invention is useful in diagnostic methods.

BACKGROUND OF THE INVENTION

There is a continuing need in medical practice, research and diagnostic procedures for rapid and accurate detection or quantification of biological and chemical substances which are present in biological fluids, cells or tissues. For example, the presence of drugs, hormones, steroids, polypeptides, nucleotides, prostaglandins, proteins, carbohydrates or infectious organisms (bacteria, fungi or viruses) in biological specimens has to b determined in an accurate and rapid fashion for suitable diagnosis or treatment.

For example, organisms classified as gram positive bacteria, such as group specific Streptococcus, are known to be pathogenic in humans. Group A organisms are primarily responsible for causing B hemolytic pneumonia, scarlet fever, rheumatic fever, cardiac sequelae, glomerulo nephritis, septic sore throat and puerpueral sepsis. Because of the serious nature of infections potentially caused by Streptococcus A, it is important to diagnose its presence at an early stage so that an appropriate course of treatment can be pursued. In other words, it is highly desirable to have a highly sensitive assay so that infectious agents can be detected at low concentration.

To provide diagnostic determinations, various methods have been devised for isolating and identifying biological or chemical substances employing specific binding reactions between the substance to be detected (identified as a "target ligand" or simply "ligand" herein) and receptors (molecules which specifically react or bind with that substance). This reaction between a ligand and its corresponding receptor is known as a specific binding reaction. Where either the ligand or receptor is an antibody, the reaction is known as an immunological reaction. More than one ligand or receptor may participate in each reaction.

Such reactions are detected in a number of ways. Generally, one or more participants in the specific binding reaction is detectably labeled. That is, it is either chosen because it is inherently detectable, or a detectable moiety (for example, an enzyme, radioisotope, chromogen or fluorogen) is incorporated therein in some manner. Many assays (for example, ELISA) today utilize enzymes as detectable moieties because of the convenience they provide in requiring minimum equipment and skills needed for the assays, as well as improved sensitivity is some cases.

One significant problem encountered in many analytical procedures which utilize specific binding reactions is the occurrence of non-specific binding reactions. For example, specific binding species, such as antibodies or antigens, may indiscriminately react with other proteins, carbohydrates or chemical or biological materials for which they are not specific. They may also react with each other and clump together thereby inhibiting specific binding with a molecule for which they have specific reactivity. In addition, if the assays are carried out using solid supports of some type (such as membranes, glass tubes, plates, beads or fibers), the specific binding species may also non-specifically bind to such materials because of the nature of chemical groups on the surfaces.

Polyamide membranes, in particular, are susceptible to non-specific interactions with specific binding species (such as antibodies). It is known that non-specific binding to solid surfaces (such as polyamides) can be minimized by coating them with proteins, such as casein or bovine serum albumin.

All of these undesired non-specific reactions cause background interference (that is, unwanted detectable signal) and poor assay sensitivity (that is, detection of low concentrations is poor). In copending and commonly assigned U.S.S.N. 098,433 (filed Sept. 18, 1987, now U.S. Pat. No. 4,828,980, by Snyder, Warren III and Nelson), it is disclosed that non-specific interactions in agglutination assays can be minimized by coating microporous membranes used in those assays with certain low pI proteins or carbohydrates. While an improvement was achieved with agglutination assays, it has been found that coating membranes similarly in non-agglutination assays, such as ELISA or sandwich assays, does not acceptably provide both low background and high assay sensitivity. Sensitivity in assays using enzyme labels is generally high, but unwanted background can be a problem even if the membrane is coated.

It is highly desirable to have assays which are highly sensitive to low concentrations of ligand but which also exhibit minimal unwanted signal from non-specific interactions.

SUMMARY OF THE INVENTION

The problems noted above are significantly overcome in assays by using a specific binding composition comprising: a specific binding species, and one or more water-soluble proteins or carbohydrates, substantially none of which has a pI greater than about 5.

This specific binding composition can be included in a diagnostic test kit for the detection of a target ligand. Where the specific binding species is enzyme labeled, the kit also comprises a dye-forming composition which is capable of providing a dye in the presence of the enzyme.

This invention also provides a method For the detection of a target ligand in a biological specimen comprising the steps of:

A. contacting a sample of a biological specimen suspected of containing a target ligand with a specific binding composition comprising:

a specific binding species and one or more water-soluble proteins or carbohydrates, substantially none of which has a pI greater than about 5, to form a specific binding complex, and B. detecting the presence of the complex as an indication of the presence of the ligand in the specimen.

The present invention provides a composition which enables one to have a highly sensitive diagnostic test using a specific binding species (for example, a labeled antibody). The improved sensitivity of the assay is accomplished by using the specific binding species in admixture with one or more water-soluble proteins or carbohydrates, substantially none of which has a pI greater than about 5. What is meant by "substantially none" is described in more detail below. These particular proteins and carbohydrates effectively reduce background in the assay without adversely affecting sensitivity as compared to the use of similar proteins and carbohydrates (such as casein or bovine serum albumin) which have higher pI values. Mixing the protein or carbohydrate with the specific binding species, as opposed to coating it on a membrane or other solid surface used in the assay, reduces the non-specific interactions of the species with itself, solid surfaces or other proteins or carbohydrates which are not of interest.

DETAILED DESCRIPTION OF THE INVENTION

The present invention can be used to rapidly detect the presence of a target ligand in a biological specimen from human or animal hosts. As noted above, this ligand can be any chemical or biological substance for which there is corresponding receptor which specifically reacts therewith to form a complex. Representative ligands include, but are not limited to, proteins (such as enzymes, antibodies and antigenic proteins and fragments thereof), peptides, polypeptides, nucleotides, carbohydrates, plant lectins, toxins, haptens, drugs, viruses, fungi and bacteria and components thereof, and other materials known to one skilled in the art. This invention is particularly useful for the detection of Streptococcal antigens, such as the carbohydrate antigens extracted from Streptococcal A, B, C or G group organisms. Streptococcal A antigen is most particularly detectable with this invention.

Biological samples which can be so assayed include, but are not limited to, whole blood or a component (serum or plasma) thereof, saliva or mucous from the throat or mouth, lacrimal fluid, spinal fluid, feces, urine, vaginal secretions, seminal fluid, human tissue or organ extracts and human milk. The specimens can be collected using suitable procedures. For example, a throat swab specimen is generally assayed in the detection of Streptococcal antigens.

The critical aspect of the present invention is the use of a specific binding composition comprising a specific binding species and one or more water-soluble proteins or carbohydrates, substantially none of which has a pI greater than about 5 (defined in detail below).

As defined herein, the specific binding species represents any biological or chemical compound which will bind specifically to another biological compound. If the species reacts specifically with the target ligand, the species is known as a receptor or that ligand. Alternatively, the species may bind specifically with a compound which is a receptor to the ligand (and not to the ligand itself). Representative specific binding species include, but are not limited to, antibodies, antigenic materials (such as proteins and carbohydrates), peptides, polypeptides, nucleotides, haptens, drugs, hormones, avidin or derivatives thereof, biotin or derivatives thereof, lectins or derivatives thereof and others known to one skilled in the art. It would be readily apparent to a skilled worker as to what specific binding species would be useful with a particular target ligand or receptor.

Preferably, the specific binding species is suitably labeled or providing a detectable signal. The label can be an inherent portion of the molecule, or a moiety specifically attached thereto. The label can be directly detectable, for example, radioisotopes, chemiluminescent moieties, phosphorescent compounds, fluorescent moieties or chromogenic moieties, which are detectable visually or using suitable equipment without further chemical reaction. Alternatively, they can be indirectly detectable, such as with labels such as enzymes, biotin or avidin, which participate in one or more reactions to provide a detectable species.

More preferably, the specific binding species is labeled with an enzyme such as, but not limited to, peroxidase, alkaline phosphatase, urease, glucose oxidase and $\beta$-glucosidase. Peroxidase and alkaline phosphatase are preferred.

Labeled specific binding species can be prepared using known procedures. Many are commercially available. Others are not commercially available, but they are prepared using known procedures (see, for example, *Methods in Enzymology*, 92. Immunochemical Techniques, p.277, Langone and Van Vunakis, Eds., 1983 for preparing radiolabeled species, E.P. Publication 201,079 and U.S. Pat. No. 4,276,206 or preparing biotinylated species). An enzyme-labeled species is generally prepared by derivatizing the enzyme, purifying the enzyme derivative, reacting the derivative with the antibody, and purification and characterization of the resulting conjugate. A number of procedures are described in the following references: Yoshitake, *Eur. J. Biochem.*, 101, 395 (1979), Nakane et al, *J. Histochemistry and Cytochemistry*, 22. 1084(1974) and Avrameas, *Bull. Soc. Chim. Biol.*, 50, 1169 (1968).

The amount of specific binding species present in the composition will vary depending upon the target ligand, the dye forming composition used (where an enzyme label is used), the particular label used and other factors of a particular assay. Generally, however, it is present in an amount of at least about 0.1 $\mu$g/ml, and preferably form about 1 to about 20 $\mu$g/ml.

The second critical component of the specific binding composition is a low pI (5 or less), water-soluble protein or carbohydrate, or mixtures thereof. The term pI (or isoelectric point) is known as the pH at which there is an equal number of positive and negative charges in a molecule so that the molecule is neutral in charge. The pI of a protein or carbohydrate can be measured using known materials and procedures. For example, it can be measured by isoelectric focusing using an LKB Ampholine PAG plate (available from LKB Produkter AB, Bromma, Sweden), pH range 3.5–9.5 and standard calibrators.

This invention is intended to include compositions having a minor amount (for example, less than about 25 weight percent of total protein and carbohydrate weight) of one or more proteins or carbohydrates having a pI above about 5. Thus, not every protein or carbohydrate in the composition must have a low pI, but it should be recognized that as more materials having high pI are used, the advantages of the invention are less pronounced. It is preferred that no proteins or carbohydrates having a pI above 5 be used in the specific binding composition.

Useful water-soluble low pI proteins include casein derivatives or other protein derivatives which are negatively charged (for example, derivatives obtained from acylation, alkylation or sulfonation of casein), such as succinylated casein, glutarylated casein, succinylated bovine serum albumin, succinylated collagen, and others apparent to one skilled in the art. These materials are readily prepared by acylating, alkylating or sulfonating a protein having available amine groups using suitable conditions. Useful acylating agents include, but are not limited to, those described in U.S. Pat. No. 4,591,571 (issued May 27, 1986 to Kuboyama et al), such as anhydrides, acyl halides and esters derived from dicarboxylic and polycarboxylic acids. Preferred acylating agents include succinic anhydride, glutaric anhydride and dimethyl glutaric anhydride. Succinic anhydride is an especially preferred acylating agent. The preparation of succinylated casein is described below.

Alkylating and sulfonating agents useful in modifying the proteins for use in this invention include, but are not limited to, bromoacetic acid, chloroacetic acid, fluoronitrobenzene, m-(chlorosulfonyl)benzoic acid, bromomalonic acid, bromopropionic acid and p-(chlorosulfonyl)benzoic acid.

Useful low pI carbohydrates include water-soluble cellulose derivatives. Representative compounds are carboxymethyl cellulose, carboxyethyl cellulose and others which would be readily apparent to one skilled in the art. These cellulose derivatives are generally available commercially.

Preferred materials used in admixture with the specific binding species are succinylated casein, glutarylated casein, carboxymethyl cellulose, succinylated bovine serum albumin and succinylated collagen. Succinylated casein is most preferred.

The water-soluble protein or carbohydrate described above is preferably present in the specific binding composition in an amount of at least about 0.05%, based on total composition weight. More preferably, it is present in an amount of from about 0.05 to about 2 weight percent.

The composition of this invention is prepared generally by mixing the specific binding species and low pI proteins or carbohydrates in a suitable buffer (pH of 4 to 9). Optional addenda include preservatives, electron transfer agents such as 4'-hydroxyacetanilide and other materials known to one skilled in the art. Example 1 shows a representative composition of this invention.

The specific binding composition of this invention can be used in any assay wherein a specific binding species is useful for detecting the presence or absence, or amount of a specific binding ligand. For example, the assay could be an immunometric assay (also known as a "sandwich" assay), competitive binding, direct or indirect attachment assay, or another known to one skilled in the art. The specific binding species in the composition can be a receptor for the ligand of interest, or it can be specifically reactive with another molecule which is such a receptor. In either case, the species can be labeled or unlabeled, and preferably, it is labeled as described above. Each assay is well exemplified in the art, and requires not further detailed description here. Useful assays can be carried out in solution, or in diagnostic test devices, analytical elements, reagent strips or other useful articles.

For exemplification purposes, the remainder of this discussion is directed to assays for ligands, such as Streptococcal antigens, using a microporous membrane as a capture and filtration means. The membrane is generally incorporated into a diagnostic test device which is capable of receiving and retaining all reagents and fluids used in the assay. But is should be understood that the invention is not limited to these specific assays or features. Reference is made to the details provided in copending and commonly assigned U.S.S.N. 206,236 of Snyder, Grogan and Sutton and entitled "Microporous Article Having a Stabilized Specific Binding Reagent, a Method for Its Use and a Diagnostic Test Kit", filed on even date herewith.

Various test devices are known in the art including those described in U.S. Pat. Nos. 3,825,410 (issued July 23, 1974 to Bagshawe), 3,888,629 (issued June 10, 1975 to Bagshawe), 3,970,429 (issued July 20, 1976 to Updike) and 4,446,232 (issued May 1, 1984 to Liotta). Particularly useful devices are described in copending and commonly assigned U.S.S.Ns. 098,248 (filed Sept. 18, 1987 by Hinckley et al), now abandoned and U.S.S.N. 136,211 (filed Dec. 18, 1987 by Smith Lewis), now U.S. Pat. No. 4,870,007 (issued Sept. 26,1989).

More specifically, the test device comprises a water-insoluble shell having one or more test wells therein each of which can accommodate a sample of a biological specimen and appropriate reagents.

The shell can be prepared from any useful water-insoluble material such as glass, polymeric materials, ceramics, fibrous materials, cellulosic materials and other materials known in the art.

In a preferred embodiment, the test device has three test wells designed for providing a specimen test result and positive and negative control results. Each test well has a microporous article mounted therein. Another test device is described and claimed in copending and commonly assigned U S.S.Ns. 019,810 (filed Feb. 27, 1987 by Hinckley), now U.S. Pat. No. 4,833,087 and 098,248 (filed Sept. 18, 1987 by Hinckley et al), now abandoned. Other variations of useful test devices would be within the purview of a worker of ordinary skill in the art.

Generally, the method of this invention is carried out by contacting a sample of a biological specimen suspected of containing a target ligand with a specific binding composition of this invention in such a manner as to form a specific binding complex directly or indirectly between the target ligand and the specific binding species. The ligand and species can be directly complexed if the species is a receptor for the ligand. Alternatively, the species may be secondarily complexed with the ligand through one or more other specific binding molecules which bind to the ligand and to each other. For example, the ligand could be complexed directly with a receptor, and the specific binding species could be reacted with the receptor also.

The contact between the ligand and species can be accomplished in any suitable manner, but preferably the specimen is mixed with the species in a test device.

Prior to, simultaneously with or subsequently to this contact, the target ligand or specific binding species can be complexed with other specific binding compounds as long as this reaction does not hinder the reaction of the species with the target ligand. Such situations could involve an immunometric assay wherein the ligand is complexed with two receptor molecules (same or different) one of which is labeled and the other is unlabeled. The unlabeled receptor can be insolubilized or capable of being insolubilized at a later point in the assay. Alternatively, the assay could be a direct binding assay wherein the ligand directly attaches to a solid support, and is reacted with a labeled receptor or an unlabeled receptor followed by reaction of the receptor with an enzyme-labeled receptor to the first receptor.

The complex formed in the assay is then detected in a suitable manner. For example, the complex could be detected visually if it forms clumps which are detectable when separated from fluid and uncomplexed materials. Preferably, the species is labeled in a suitable manner, and appropriate equipment and reagents are used to produce a detectable signal. Radioisotopic labels can be detected by measuring the counts per minute in the complexed material. Other labels may require some reagents and reactions to produce a dye, chemiluminescent or other signal.

More preferably, the complex is detected using an enzyme label and an appropriate dye providing composition comprising appropriate reagents which react with the enzyme to provide a dye. The type of label will determine the reagents to be used to provide the dye, and one skilled in the art would readily know how to design the appropriate dye providing composition. The dye can be provided through a single reaction of enzyme with a substrate, or through a series of reactions.

The resulting dye can be observed visually or measured using suitable spectrophotometric equipment.

Peroxidase is a preferred enzyme label, and a number of suitable dye forming compositions are known comprising a substrate or substrate forming reactants as well as dye forming reactants. The substrate itself can be a dye forming compound, such as benzidine, tetramethylbenzidine or other benzidine derivatives, 2,2'-azino-di-(3-ethyl-benzthiazolone -6-sulfonic acid), phenol red, o-phenylenediamine, pyrogallol, 4-aminoantipyrine, bromopyrogallol red and others known in the art. Alternatively, a hydrogen donor and an electron acceptor can be combined to provide a detectable species (for example, see U.S. Pat. No. 4,260,679).

Preferably, the dye forming composition includes a leuco dye which provides a dye in the presence of hydrogen peroxide and peroxidase [for example, a triarylimidazole leuco dye as described in U.S. Pat. Nos. 4,089,747 (issued May 16, 1978 to Bruschi) or a triarylmethane leuco dye as described in U.S. Pat. No. 4,670,385 (issued June 2, 1987 to Babb et al)]. A preferred dye providing composition is described and claimed in copending and commonly assigned U.S.S.N. 136,166, filed Dec. 18, 1987 by McClune and Bishop.

The diagnostic test kit of this invention includes an enzyme labeled specific binding composition of this invention as well as an appropriate dye providing composition. These kit components can be packaged in a suitable manner and included in a carrier of some type which can be compartmentalized to receive the vials or bottles of liquid or solid reagents. In addition, it can also include one or more of the following which are useful in carrying out the method: test device, extraction reagents (if the ligand must be extracted before the assay), wash solutions, diluents, further receptor molecules and other reagents known to one skilled in the art for a given assay. Reagents can be provided in dry form or in appropriate solutions. Non reactive components of the kit can include instructions, mixing vessels, stirring means, pipettes and the like.

The following examples are representative of the practice of this invention but are not intended to limit it.

MATERIALS

A leuco dye solution was prepared with 2-(4hydroxy-3,5 dimethoxyphenyl)-4,5-bis(4-methoxyphenyl)imidazole as follows:

Solid leuco dye to make a 0.1% solution) was dissolved in a solution of 20% poly(vinylpyrrolidone) in sodium phosphate buffer (5 mmolar). This solution was then added to a solution containing hydrogen peroxide (10 mmolar), 4'-hydroxyacetanilide electron transfer agent (0.7 mmolar) and diethylenetriaminepentaacetic acid chelating agent (10 μmolar in sodium phosphate buffer to produce a final concentration of 1% poly(vinylpyrrolidone) and 0.005% leuco dye. This composition is described and claimed in copending and commonly assigned U.S.S.N. 206,258 filed on even date herewith by Snyder et al and entitled "Imidazole Leuco Dye Composition Containing 4'-Hydroxyacetanilide, Diagnostic Kit and Method Using Same".

Succinylated casein was prepared by reacting casein with an equal weight of succinic anhydride for four hours at 25° C., then purifying the product by dialysis.

The buffers mentioned and used herein are available from a number of commercial sources including Sigma Chemical Co.

LoProdyne ® nylon microporous membranes were obtained from Pall Corp., incorporated into the test wells of a disposable test device and pretreated with Fluorad FC 135 surfactant (0.05 g/m² available from 3M Co.).

EXAMPLE 1

SPECIFIC BINDING COMPOSITION

This example illustrates a preferred specific binding composition prepared according to this invention. This composition contained an anti Streptococcus A-peroxidase labeled conjugate which was prepared using immunopurified rabbit polyclonal antibodies obtained commercially and horseradish peroxidase from Miles Laboratories (Elkhart, Indiana by the method described by Yoshitake et al, *Eur. J. Biochem.* 101, 395 (1979). Mixed with the conjugate (9 μg/ml) were succinylated casein (pI 4.5, 0.5–1.5% by weight), 0.1 molar 4-morpholinopropane sulfonic acid buffer (pH 7.5), 10 mmolar 4'-hydroxyacetanilide and 0.01% by weight of preservative.

EXAMPLE 2

ASSAY FOR STREPTOCOCCUS A ANTIGEN

This example demonstrates the use of the composition of Example 1 in the method of this invention to detect Streptococcus A antigen in a biological specimen.

Streptococcus A antigen was obtained from Group A strep cultures using a standard nitrous acid extraction procedure wherein aqueous sodium nitrite was mixed with an acidic coreagent prior to the addition of the cultured organism. The extraction fluid was then neutralized by the addition of excess buffer. The Group A carbohydrate antigen was obtained using acidic ethanol and acetone, discarding the supernatant and resuspending the pellet in 0.85% saline solution. The concentration of rhamnose was determined by the method of Dische and Shattles, *J. Biol Chem.* 175, 595–603 (1948). This concentration was resuspended in a neutralized extraction fluid comprising citric acid (10 μl, 1.2 molar), sodium nitrite (120 μl, 8 molar and 4-morpholinopropane sulfonic acid buffer (120 μl, 1 molar, pH 7.5).

A microporous membrane as described above was incorporated into each of the three test wells of two disposable test devices which were similar to that described in U.S.S.N. 098,248 (noted above). A dispersion of the specific binding reagent comprising poly[styrene-co-m & p-(2-chloroethylsulfonylmethyl)styrene] beads [2 μl of a 1% solid suspension containing poly(acrylamide) (5% by weight in 0.1 molar glycine, pH 8.5) and 0.0005%, by weight, of an optical brightener], was added to the center area of the membrane in the test well identified as the specimen test well. To the beads were covalently bound rabbit polyclonal antibodies to Streptococcus A antigen.

A second test well, considered the negative control well, contained a dried dispersion (2 μl) of the same polymeric beads to which had been attached rabbit gamma globulin (1%, by weight) admixed with poly(acrylamide) (5% by weight in glycine buffer) and the optical brightener. This dispersion was applied in a center area of the membrane.

A third test well, considered the positive control well, contained a dried dispersion of the reagent (2 μl) described above in poly(acrylamide) (5% by weight in glycine buffer), the optical brightener and 20 ng/ml of the Streptococcus A antigen. This dispersion was applied in a center area of the membrane.

Two-hundred microliters of the antigen extract solution was added to the specimen test well only and allowed to flow through.

A solution containing the peroxidase labeled-conjugate described above in Example 1 (40 μl) was added to all wells and allowed to flow through. The disposable was then incubated at room temperature for one to two minutes.

The wells were filled with a wash solution containing sodium decyl sulfate (70 mmolar) in sodium phosphate buffer (0.1 molar, pH 7.2) was applied to all wells and allowed to flow through.

The leuco dye solution described above (120 μl) was added to all wells, and after two minutes incubation at room temperature, the resulting color was measured in the test wells. The specimen well to which the extracted antigen had been applied showed a red area in the center of the well with a distinct undyed area around it. The positive control well showed a red color while the negative control well showed no color. This indicates a successful detection of the antigen by the assay.

EXAMPLE 3

COMPARATIVE EXAMPLE USING SEVERAL PROTEINS WITH THE LABELED ANTIBODIES

Streptococcus A antigen was obtained as described in Example 2.

A disposable device containing a membrane as described above was used in the assays. In the center area of the test well was added a suspension (2 μl, 1% solids) of the polymeric beads like those used in Example 2 admixed with poly(acylamide) (5% by weight in glycine buffer, 0.1 molar, pH 8.5). Following this, a sample of extracted antigen (200 μl, 2 9 ng/ml) was added to the test well.

Four different compositions of specific binding species were tested in this example:

(1) Anti Streptococcus A antibodies (9 μg/ml) conjugated to horseradish peroxidase, 0.5% by weight) succinylated casein (pI 4.5) in 4-morpholinopropane sulfonic acid (0.1 molar), 4'-hydroxyacetanilide (10 mmolar) and 0.1% (by weight) thimerosal preservative.

(2) Same as composition (1) except that casein (pI above 5) was used in place of succinylated casein.

(3) Same as composition (1) except that bovine serum albumin (pI above 5) was used in place of succinylated casein.

(4) Same as composition (1) but lacking succinylated casein.

Each composition (40 μl) was added to the test well of the test device and incubated for 2 minutes at room temperature. The membranes were then washed with a wash composition comprising sodium decylsulfate (1.8 weight %) in sodium phosphate buffer (0.1 molar, pH 7.2).

The leuco dye composition 40 μl) described in Example 2 was added, and the disposable was incubated for 2 minutes at room temperature, followed by measurement of the reflection density using a spectrophotometer. The reflection density was converted to transmission density ($D_T$) and the results are shown in the following table.

TABLE

| Composition | $D_T$ Test | Background |
|---|---|---|
| (1) | 0.101 | 0.005 |
| (2) | 0.024 | 0.005 |
| (3) | 0.089 | 0.026 |
| (4) | 0.185 | 0.185 |

The data indicate that only composition (1) containing succinylated casein provides greatest sensitivity (highest dye signal with the lowest background.

Comparison with Assay Using Membrane Coated with Low pI protein

A test assay was carried out similar to Example 2 for the detection of Streptococcus A antigen using the teachings of U.S.S.N. 098, 433, (noted above), now U.S. Pat. No. 4,828,980, wherein the membrane used in the assay is pretreated with a low pI protein.

The membrane was commercially obtained from Pall Crop. as an Immunodyne ® nylon microporous membrane. It was coated with succinylated casein.

The assay results provided a $D_T$ of 0.101, but the background was similarly high ($D_T$ of 0.037). This indicates that putting the low pI protein or carbohydrate on the membrane is not as desirable as adding it to the labeled specific binding species composition.

The invention has been described in detail with particular reference to preferred embodiments thereof, but it will be understood that variations and modifications can be effected within the spirit and scope of the invention.

We claim:

1. A specific binding composition consisting essentially of an aqueous mixture of a specific binding species and one or more water-soluble proteins or carbohydrates, substantially none of which has a pI greater than about 5,
said species being detectably labeled with an enzyme.

2. The composition of claim 1 wherein said water-soluble protein or carbohydrate is succinylated casein, glutarylated casein, carboxymethyl cellulose, succinylated bovine serum albumin or succinylated collagen.

3. The composition of claim 1 wherein said water-soluble protein is succinylated casein.

4. The composition of claim 1 wherein said species is an enzyme-labeled antibody.

5. The composition of claim 1 wherein said enzyme label is peroxidase, urease, glucose oxidase, alkaline phosphatase or β-glucosidase.

6. The composition of claim 1 wherein said water-soluble protein or carbohydrate is present in an amount of from about 0.05 to about 2 percent based on total composition weight.

7. The composition of claim 1 wherein said species is present in an amount of from about 0.1 to about 20 μg/ml.

8. An immunoreactive composition useful for the determination of Streptococcus A antigen and consisting essentially of an aqueous mixture of an enzyme-labeled antibody to Streptococcus A antigen and one or more water-soluble proteins or carbohydrates, substantially none of which has a pI greater than about 5.

9. The composition of claim 8 wherein said enzyme label is peroxidase or alkaline phosphatase.

10. The composition of claim 8 wherein said water-soluble protein or carbohydrate is succinylated casein, glutarylated casein, carboxymethyl cellulose, succinylated bovine serum albumin or succinylated collagen.

11. A diagnostic test kit for the detection of a target ligand, said kit comprising, separately packaged:
   a. a specific binding composition consisting essentially of an aqueous mixture of an enzyme-labeled specific binding species which is reactive with said ligand or with a receptor for said ligand, and one or more water-soluble proteins or carbohydrates, substantially none of which has a pI greater than about 5, and
   b. a dye-forming composition which is capable of providing a dye in the presence of said enzyme.

12. The test kit of claim 11 wherein said species is labeled with peroxidase, and said dye-forming composition comprises a leuco dye capable of providing a dye in the presence of peroxidase and hydrogen peroxide.

13. The test kit of claim 11 wherein said water-soluble protein or carbohydrate is succinylated casein, glutarylated casein, carboxymethyl cellulose, succinylated bovine serum albumin or succinylated collagen.

14. A method for the detection of a target ligand in a biological specimen comprising the steps of:
   A. contacting a sample of a biological specimen suspected of containing a target ligand with a specific binding composition comprising an aqueous mixture of:
      a specific binding species for said ligand or for its receptor, and one or more water-soluble proteins or carbohydrates, substantially none of which has a pI greater than about 5,
      said species being detectably labeled with a label selected from the group consisting of radioisotopes, chemiluminescent moieties, phosphorescent compounds, fluorescent moieties, chromogenic moieties, enzymes, avidin and biotin,
      to form a detectably labeled specific binding complex between said ligand and said detectably labeled species, and
   B. detecting the presence of said complex as an indication of the presence of said ligand in said specimen.

15. The method of claim 14 wherein, prior to, simultaneously with or subsequent to said contacting step A, contacting said ligand with an second receptor for said ligand which is insolubilized.

16. The method of claim 14 wherein, prior to said contacting step A, said ligand is contacted with an unlabeled receptor therefor, and said specific binding composition comprises an enzyme-labeled specific binding species specifically reactive with said unlabeled receptor.

17. A method for the detection of Streptococcus A in a biological specimen comprising the steps of:
   A. contacting a sample of a biological specimen suspected of containing extracted Streptococcus A antigen with a specific binding composition comprising an aqueous mixture of an enzyme-labeled antibody to Streptococcus A antigen and one or more water-soluble proteins or carbohydrates, substantially none of which has a pI greater than about 5,
      to form an enzyme-labeled specific binding complex, and
   B. detecting the presence of said complex as an indication of the presence of Streptococcus A in said specimen.

18. The method of claim 17 wherein said water-soluble protein or carbohydate is succinylated casein, glutarylated casein, carboxymethyl cellulose, succinylated bovine serum albumin or succinylated collagen.

* * * * *